US008026665B2

United States Patent
Kim et al.

(10) Patent No.: US 8,026,665 B2
(45) Date of Patent: Sep. 27, 2011

(54) DEUTERATED ARYL AMINE COMPOUND, PREPARATION METHOD THEREOF, AND ORGANIC LIGHT EMITTING DIODE USING THE SAME

(75) Inventors: Kyoung-soo Kim, Daejeon (KR); Tae-hyung Kim, Yongin (KR); Kyu-man Youn, Suwon (KR); Hyeon-jin Seo, Donghae (KR); Myung-soo Ko, Seoul (KR); Sang-hoon Lee, Yongin (KR); Dong-wan Ryu, Yongin (KR); Yeong-eun Kim, Incheon (KR)

(73) Assignee: Doosan Corporation, Seoul (KR)

( * ) Notice: Subject to any disclaimer, the term of this patent is extended or adjusted under 35 U.S.C. 154(b) by 912 days.

(21) Appl. No.: 11/913,683

(22) PCT Filed: Nov. 18, 2005

(86) PCT No.: PCT/KR2005/003926
§ 371 (c)(1),
(2), (4) Date: Nov. 6, 2007

(87) PCT Pub. No.: WO2006/121237
PCT Pub. Date: Nov. 16, 2006

(65) Prior Publication Data
US 2008/0191614 A1    Aug. 14, 2008

(30) Foreign Application Priority Data
May 7, 2005    (KR) .......................... 10-2005-0038221

(51) Int. Cl.
*H01L 51/54*    (2006.01)
*C09K 11/06*    (2006.01)

(52) U.S. Cl. ... 313/504; 313/506; 257/40; 257/E51.051; 428/690; 428/917

(58) Field of Classification Search .................. None
See application file for complete search history.

(56) References Cited

U.S. PATENT DOCUMENTS

| 6,541,129 | B1 | 4/2003 | Kawamura et al. |
| 6,699,599 | B2 | 3/2004 | Li et al. |

FOREIGN PATENT DOCUMENTS

| EP | 1 029 909 A1 | 8/2000 |
| JP | 11-111458 A2 | 4/1999 |
| JP | 2000-309566 A | 11/2000 |
| JP | 2003-212977 A | 7/2003 |
| JP | 2005-015419 A | 1/2005 |
| JP | 2005-048004 A | 2/2005 |
| WO | WO 02/20460 A1 | 3/2002 |
| WO | WO 2004/041774 | 5/2004 |
| WO | WO 2004/101491 A1 | 11/2004 |

OTHER PUBLICATIONS

Laeter et al., Pure and Applied Chemistry, (2003), vol. 75, No. 6, pp. 683-800.*
Japanese Office Action issued in corresponding JP Application No. 2008-511037, dated Oct. 12, 2010.

* cited by examiner

*Primary Examiner* — Angela Ortiz
*Assistant Examiner* — Brett A Crouse
(74) *Attorney, Agent, or Firm* — Sughrue Mion, PLLC

(57) ABSTRACT

Disclosed are a novel deuterated aryl amine compound capable of enhancing thermal stability, hole transporting capability, luminescence efficiency, etc. of an organic light emitting diode at the time of being used as a hole-injecting layer, a preparation method thereof, and an organic light emitting diode using the same.

3 Claims, 4 Drawing Sheets

[Fig. 1]
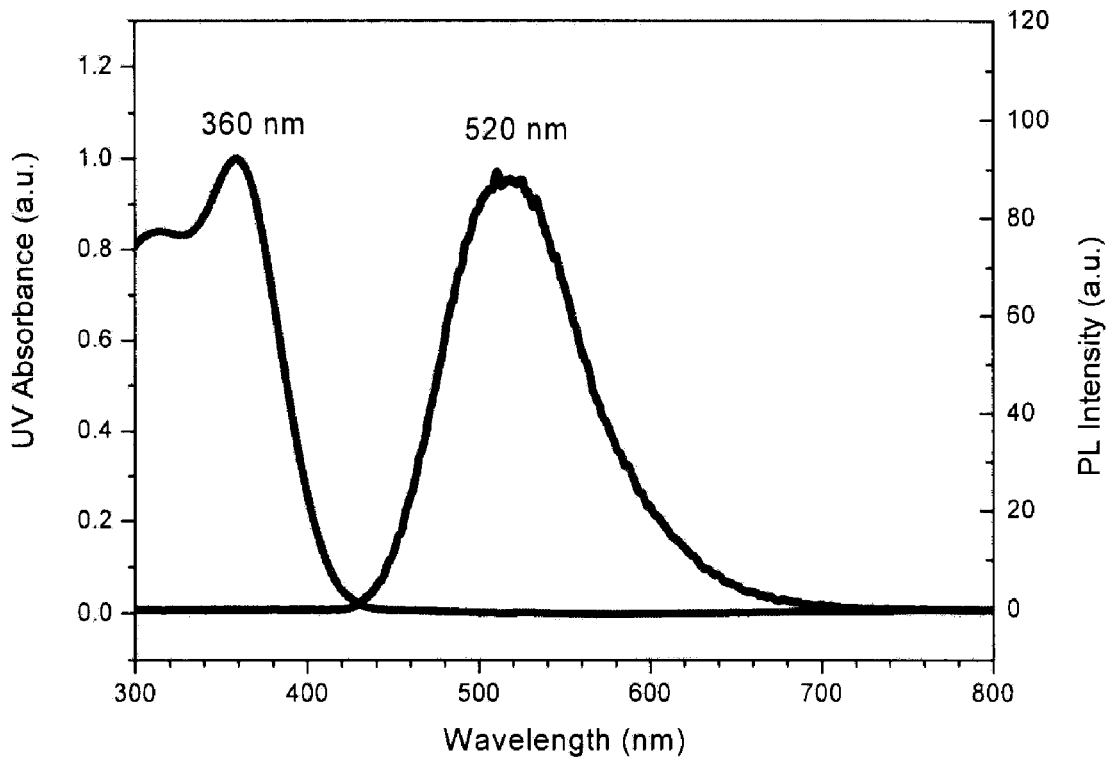
[Fig. 2]
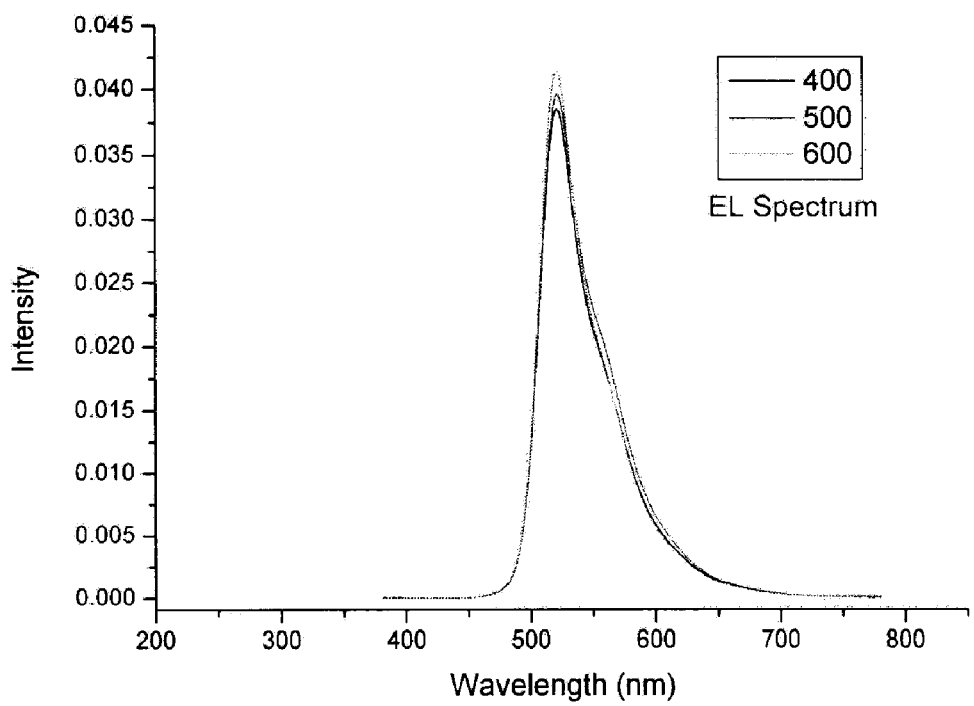

[Fig. 3]
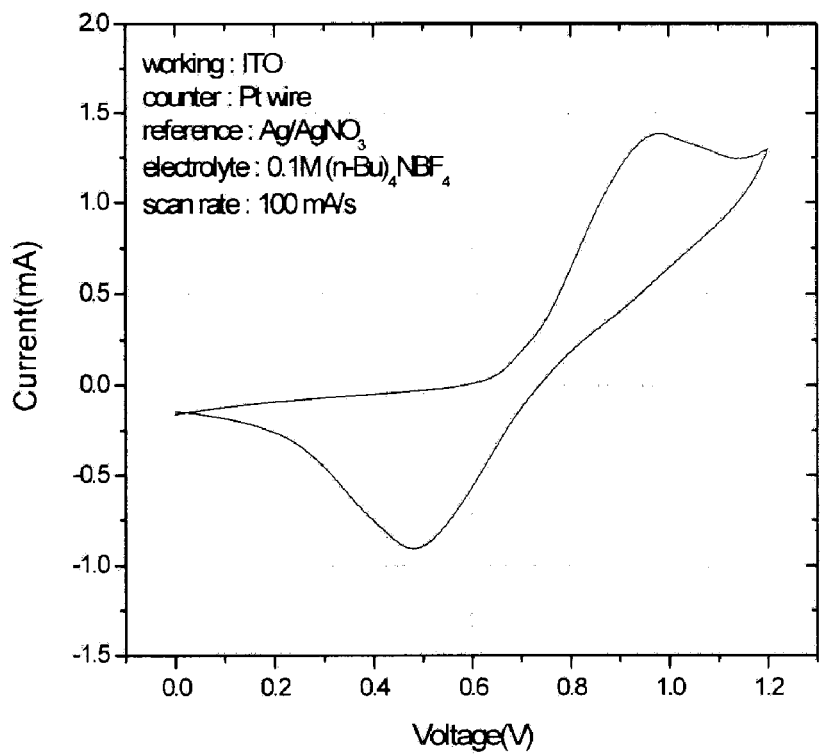
[Fig. 4]
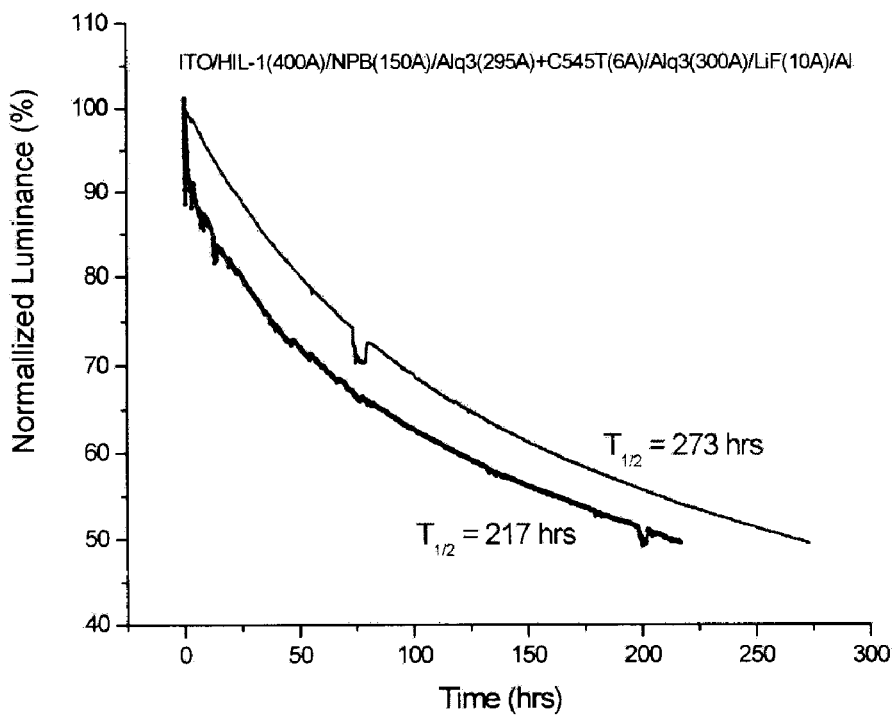

[Fig. 5]
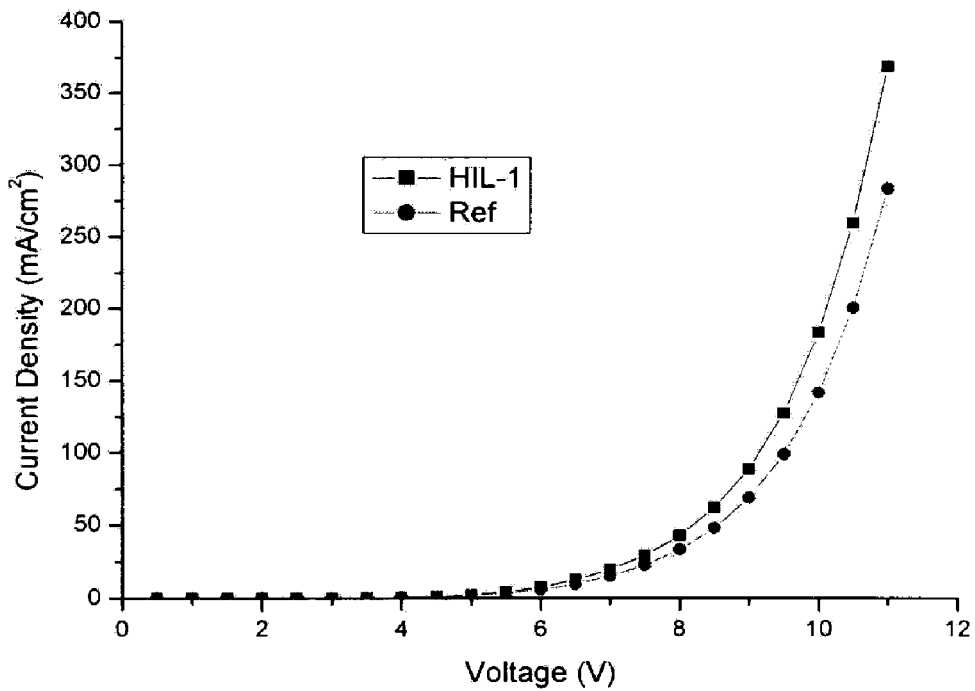
[Fig. 6]
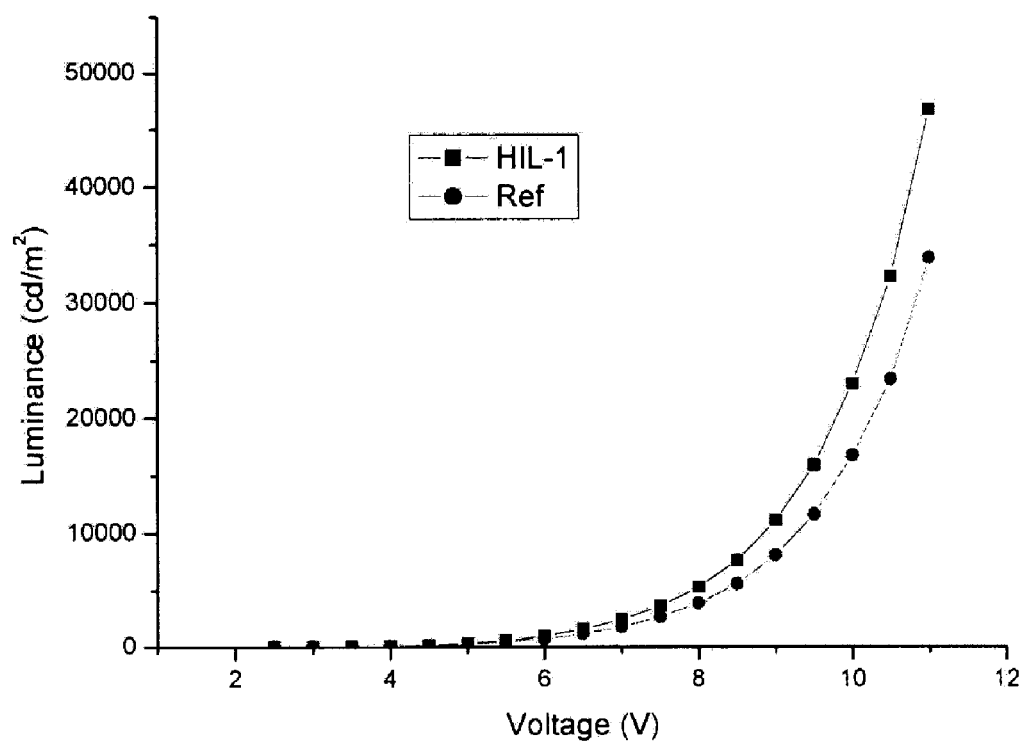

[Fig. 7]
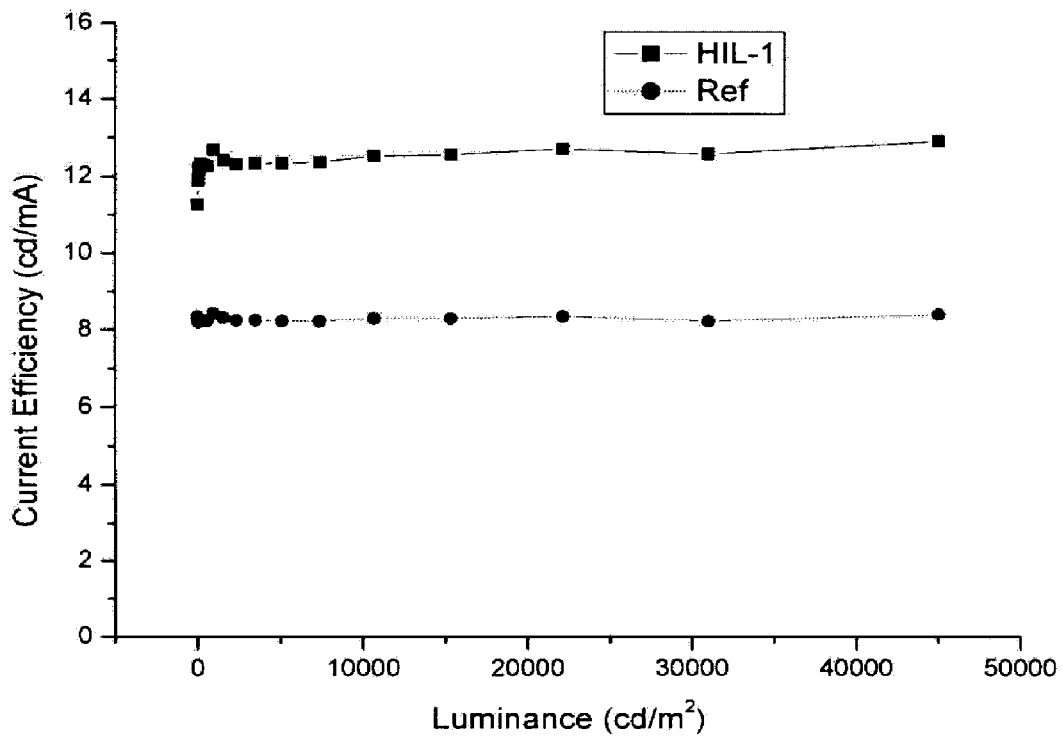
[Fig. 8]
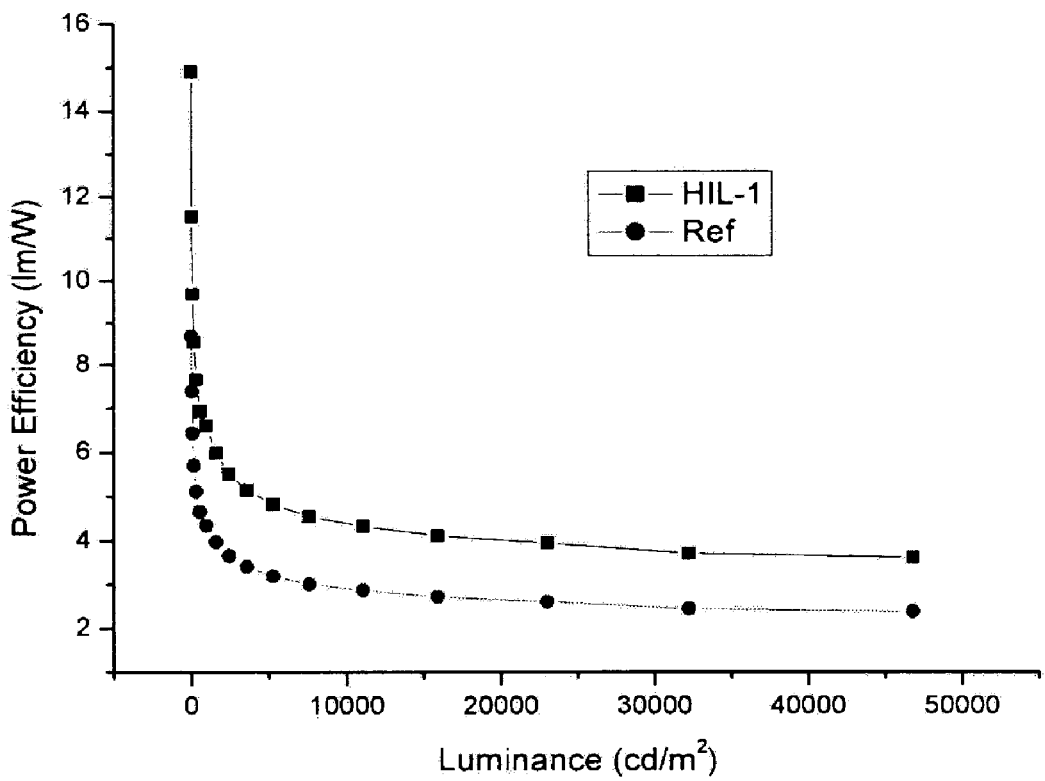

DEUTERATED ARYL AMINE COMPOUND, PREPARATION METHOD THEREOF, AND ORGANIC LIGHT EMITTING DIODE USING THE SAME

This is a National Stage Application under 35 U.S.C. §371 of PCT/KR2005/003926 filed Nov. 18, 2005, which claims priority to Korean Patent Application No. 10-2005-0038221 filed May 7, 2005.

TECHNICAL FIELD

The present invention relates to a novel deuterated aryl amine compound capable of being used as a hole-injecting layer of an organic light emitting diode, a preparation method thereof, and an organic light emitting diode using the same.

BACKGROUND ART

A lot of materials for an electro-luminescence device have been developed continuously since Tang first developed an electro-luminescence device by a vacuum deposition method in 1987. However, the luminance and thermal stability of the commercialized electro-luminescence device becomes lower when used for a long time, and thus, it is necessary to be improved.

Korean Patent Publication No. 2002-62940 discloses some materials for an organic light emitting diode of an aryl amine compound represented by the following general formula:

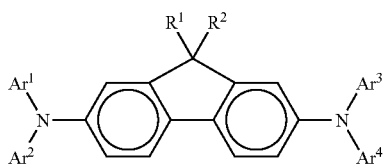

U.S. Pat. No. 6,699,599 discloses a light emitting material, in which some or all of hydrogen atoms of Ir(ppy)$_3$ are substituted with deuterium.

In general, when hydrogen is substituted with deuterium, an exciton is more easily generated, resulting in improved luminance efficiency. The reason is as follows. Since the bond strength between carbon and deuterium is stronger than that between carbon and hydrogen, the bond length between carbon and deuterium is shorter than that between carbon and hydrogen when hydrogen is substituted with deuterium. As the result, the Van der Waals force becomes smaller, by which the higher luminance efficiency can be obtained. However, U.S. Pat. No. 6,699,599 as mentioned above does not describe the extent to which the luminescent efficiency has been improved when hydrogen atoms of Ir(ppy)$_3$ are substituted with deuterium atoms.

DISCLOSURE OF INVENTION

Technical Solution

Therefore, an object of the present invention is to provide a novel deuterated aryl amine compound capable of enhancing thermal stability, luminescence efficiency, luminance, current efficiency, power efficiency, etc. at the time of being used as a hole-injecting layer of an organic light emitting diode, a preparation method thereof, and an organic light emitting diode using the same.

The foregoing and other objects, features, aspects and advantages of the present invention will become more apparent from the following detailed description of the present invention when taken in conjunction with the accompanying drawings.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings:

FIG. 1 shows UV and PL spectra of the compound HIL-1 prepared in Example 1 of the present invention;

FIG. 2 is an EL spectrum of a device fabricated using the compound HIL-1 prepared in Example 1 as a material of a hole-injecting layer;

FIG. 3 shows an energy level of the compound HIL-1 prepared in Example 1 (Eg: 3.3 eV, HOMO: 5.1 eV, LOMO: 1.8 eV)

FIG. 4 shows the lifetime of the light emitting device fabricated using the compound HIL-1 prepared in Example 1 as a material of a hole-injecting layer;

FIG. 5 shows a voltage-current density curve of the device fabricated using the compound HIL-1 prepared in Example 1 as a material of a hole-injecting layer;

FIG. 6 shows a voltage-luminance curve of the device fabricated using the compound HIL-1 prepared in Example 1 as a material of a hole-injecting layer;

FIG. 7 shows a luminance-current efficiency curve of the device fabricated using the compound HIL-1 prepared in Example 1 as a material of a hole-injecting layer.

FIG. 8 shows a luminance-power efficiency curve of the device fabricated using the compound HIL-1 prepared in Example 1 as a material of a hole-injecting layer.

MODE FOR THE INVENTION

Reference will now be made in detail to the preferred embodiments of the present invention, examples of which are illustrated in the accompanying drawings.

In general, an organic light emitting diode is constructed as a thin film having a multi-layer structure, for the reason that an interface between an electrode and an organic material can be stabilized, or that in order to overcome the transporting rate difference between a hole and an electron in the case of an organic material, an appropriate hole transporting layer and an electron transporting layer are used, thereby making the holes and the electrons into the light emitting layer properly transported to light emitting layer and making the density of the holes and electrons balanced in a light emitting layer, by which a luminescence efficiency of the organic light emitting diode can be enhanced. Accordingly, the roles of the injecting/transporting layers of holes and injecting/transporting layers of electrons are very important.

Even though hydrogen atoms present in an organic light emitting diode are substituted with deuterium, most of the chemical properties thereof are rarely changed. However, because the atomic weight of deuterium is twice as that of hydrogen, important physical properties can be changed if hydrogen atoms are substituted with deuterium atoms. Namely, in a heavy atom, its zero point energy is lowered due to its lower potential energy level and its vibration energy level is also lowered due to its smaller vibration mode. Accordingly, if hydrogen atoms are substituted with deuterium atoms existing in a compound, van der Waals' force decreases, and proton efficiency decrease due to intermolecular collision by vibration can be prevented.

The present invention was completed based on the above recognition, and relates to a novel deuterated aryl amine compound capable of enhancing thermal stability, luminescence efficiency, luminance, current efficiency, power efficiency, etc. at the time of being used as a hole-injecting layer or a light emitting layer of an organic light emitting diode, a preparation method thereof, and an organic light emitting diode using the same.

The novel deuterated aryl amine compound of the present invention are represented by the following Formula 1, comprising at least one deuterium atom per molecule.

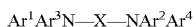   Formula 1

In Formula 1, $Ar^1$ and $Ar^2$ are respectively a diphenylaminophenyl group represented by the following Formula 2, which are identical to or different from each other.

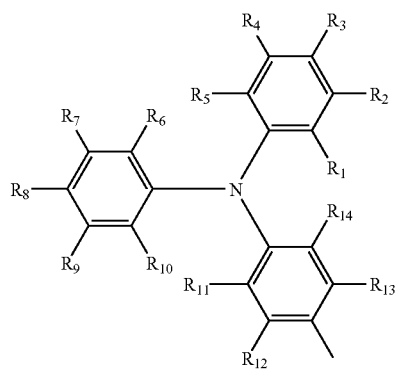

Formula 2

In Formula 1, $Ar^3$ and $Ar^4$ are respectively a naphthyl group represented by the following Formula 3, which are identical to or different from each other.

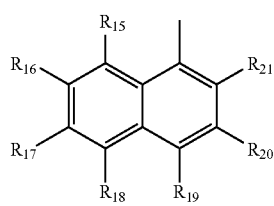

Formula 3

In Formulae 2 and 3, the $R_1$ to $R_{21}$ are respectively selected from the group consisting of hydrogen, deuterium, $C_1$-$C_{30}$ alkyl group and a halogen atom, provided that at least one of $R_1$ to $R_{21}$ are deuterium; and halogen atom is F, Cl, Br or I.

In Formula 1, X is selected from the groups having structures shown in Formula 4 below, which may be unsubstituted or substituted with at least one deuterium.

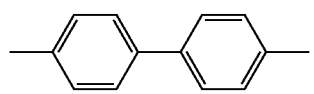

Formula 4

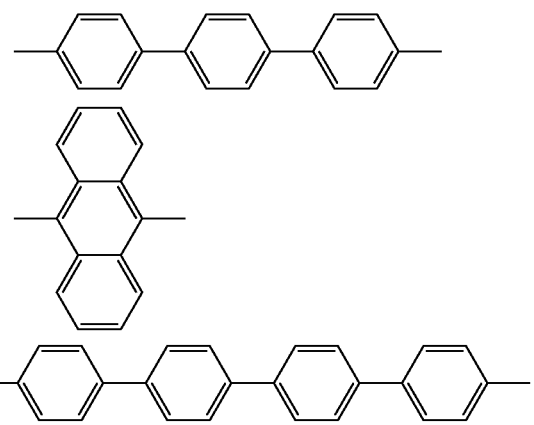

-continued

Hereinafter, a method for preparing the deuterated aryl amine compound according to the present invention will be described.

The compound of Formula 1 can be obtained by reacting compounds represented by a general formula $Ar^1$—Y and $Ar^2$—Y with compound represented by the following Formula 5.

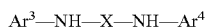   Formula 5

The compounds represented by the general formula $Ar^1$—Y and $Ar^2$—Y can be obtained by reacting a compound of Formula 6 with a compound of Formula 7a and/or 7b, and then by halogenating the obtained product with chlorine, bromine or iodine.

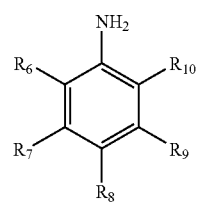

Formula 6

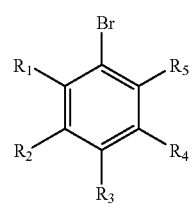

Formula 7a

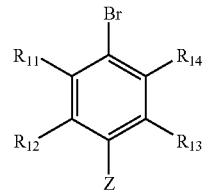

Formula 7b

The compound of Formula 5 can be obtained by reacting any one compound shown in Formula 8 below with a compound represented by Formula 9.

Formula 8

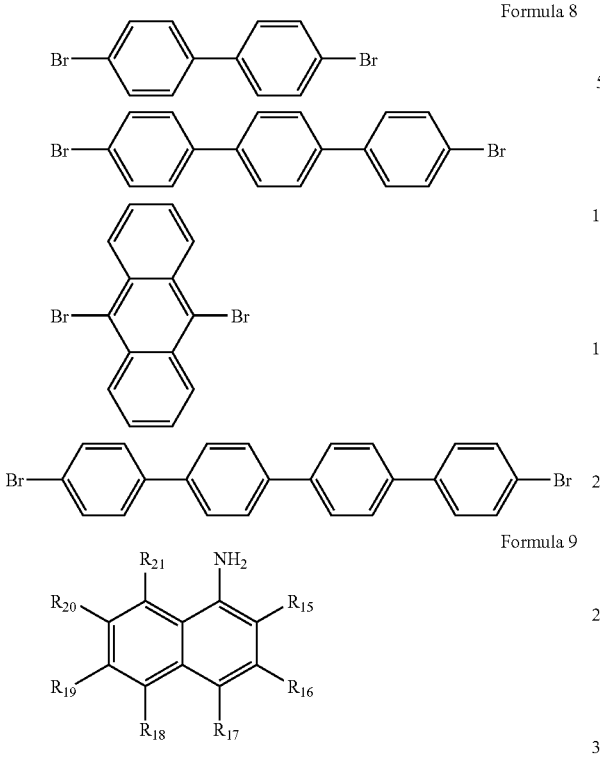

Formula 9

In the above general formulae Ar¹—Y and Ar²—Y and Formulae 5 to 9, the Ar¹, Ar², Ar³, Ar⁴, $R_1$ to $R_{21}$ and X are respectively the same as defined in Formulae 1 to 3 above; Y is a halogen atom selected from F, Cl, Br and I; and Z is hydrogen or deuterium.

EXAMPLES

Hereinafter, the present invention will now be described in detail with reference to the following examples. However, such examples are exemplary for the present invention, and accordingly, the scope of the present invention will not be limited thereto.

Example 1

(1) Preparation of triphenylamine-d15

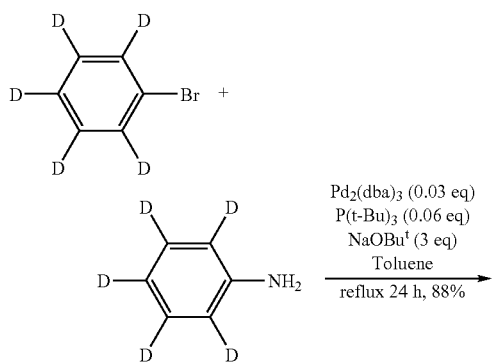

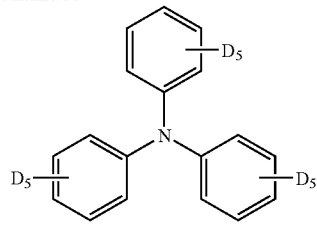

After, 5 g (30.9 mmol) of bromobenzene-d5 and 1.52 g (15.5 mmol) of aniline-d5 were dissolved in 150 mL of toluene, 0.43 g (0.465 mmol) of tris(dibenzylidene acetone dipalladium) was added thereto under a nitrogen atmosphere. To the resulting mixture, 1.79 g (18.6 mmol) of NaOBu$^t$, followed by 0.19 g (0.93 mmol) of (t-Bu)$_3$P were added. The resulting mixture was refluxed while stirring for 12 hours. The completion of the reaction was identified by a TLC. After the reaction was completed, the temperature was lowered to room temperature. The reaction solution was poured onto a thin silica pad so as to perform a short chromatography, and the fraction containing the desired product was washed with dichlorometane. The residual solution was evaporated under a reduced pressure to remove the solvent. The residue was then purified by a chromatography using 10% dichlorometane in n-hexane, to obtain 3.55 g (yield: 88%) of triphenylamine-d15 as a white solid.

(2) Preparation of (4'-iodophenyl)-diphenylamine-d14

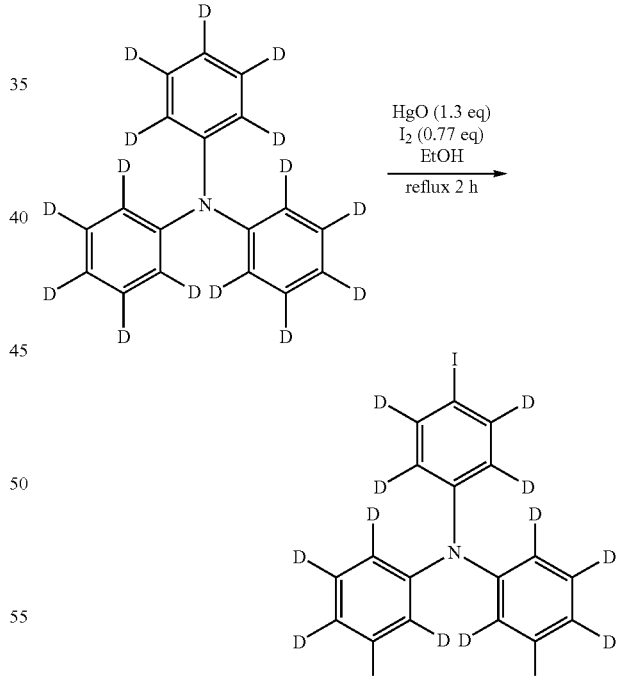

3.55 g (13.6 mmol) of the triphenylamine-d15 obtained in step (1) of Example 1 was put into 130 mL of ethanol, and the temperature was then increased to 60° C. To the resulting solution while being maintained at 60° C., 3.84 g (17.7 mmol) of mercuric oxide was added, and then 2.7 g (10.5 mmol) of I$_2$ was added in several portions. The reaction mixture was then refluxed while stirring for 2 hours. The reaction mixture was filtered by a short silica pad at a high temperature, and then was washed with acetone. The residue was evaporated to remove the solvent under a reduced pressure. The residual yellow gel was then purified by a chromatography using 10% dichlorometane/n-hexane to obtain 3.46 g (yield: 66%) of (4'-iodophenyl)-diphenylamine-d14 as a pale yellow gel.

(3) Preparation of N,N-di-naphtalen-1-yl-terphenyl-4,4'-diamine-d12

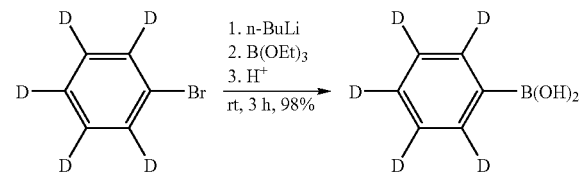

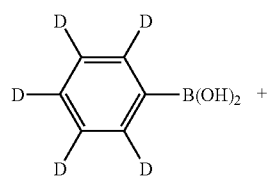

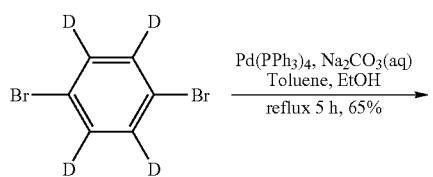

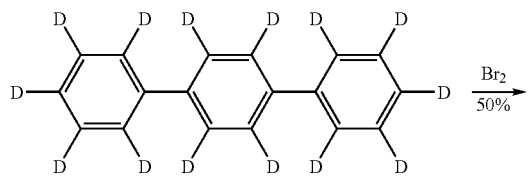

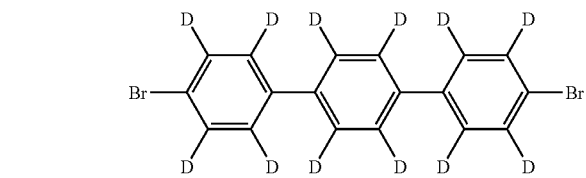

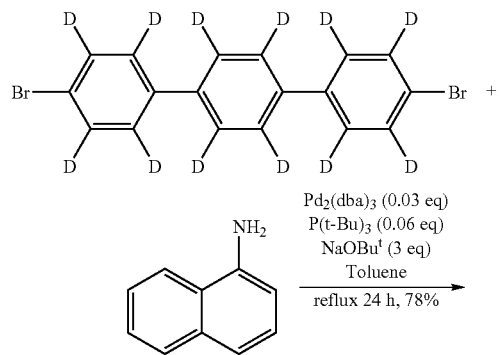

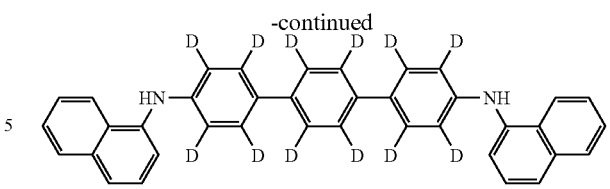

10 g (61.7 mmol) of bromobenzene-d5 was dissolved in 300 mL of tetrahydrofuran, and then the temperature of the reaction solution was maintained at −78° C. 57.8 mL (92.6 mmol) of 1.6M n-BuLi was then slowly added thereto, and the resulting solution was refluxed while stirring for at −78° C. 1 hour, to which 21 mL (123.4 mmol) of tri-ethylborate was slowly added. The reaction mixture was allowed to reach to room temperature, and then stirred for 3 hours. After 1N HCl was added to the reaction mixture at 0° C., the reaction mixture was stirred for additional one hour at room temperature. After the reaction mixture was extracted with ethyl acetate, organic layers were dried with MgSO$_4$ and then filtered. The filtrate was concentrated, thereby obtaining 7.7 g (yield: 98%) of the desired compound, phenylboronic acid-d5, as a pale yellow solid.

7.7 g (60.6 mmol) of the phenylboronic acid-d5 and 7.3 g (30.3 mmol) of 1,4-dibromobenzene-d4 were dissolved in a mixture of 60 mL of toluene and 30 mL of ethanol. To the resulting solution, 1.05 g (0.91 mmol) of tetrakis(triphenylphosphine palladium), followed by 31 mL of 2M sodium carbonate (2 mmol) were added. The reaction mixture was refluxed while stirring for 5 hours, and then cooled down to room temperature. After the reaction mixture was extracted with ethyl acetate, organic layers were dried with MgSO$_4$ and then filtered. The filtrate was concentrated and purified by a chromatography, thereby obtaining 4.8 g (yield: 65%) of terphenyl-d14 as a pale yellow solid.

4.8 g (19.6 mmol) of the terphenyl-d14 was contacted with 7.5 g (47.0 mmol) of bromine vapor for 24 hours, and then 30 mL of benzene was added thereto. The reaction mixture was filtered and then maintained at 15° C. so as to generate a crystal. The generated solid was filtered to obtain 3.9 g (yield: 50%) of dibromoterphenyl-d12 as a yellow liquid.

3.9 g (9.75 mmol) of the dibromoterphenyl-d12 and 2.79 g (19.5 mmol) of 1-aminonaphtalene were dissolved in 120 mL of toluene, and then 0.27 g (0.293 mmol) of tris(benzylideneacetonedipalladium) was added thereto under a nitrogen atmosphere. To the resulting mixture, 0.12 g (0.586 mmol) of P(t-Bu)$_3$, followed by 1.12 g (11.7 mmol) of NaOBu$^t$ were added. The reaction solution was refluxed while stirring for 24 hours. When the reaction was completed, the reaction solution was filtered at a high temperature through a thin silica gel pad to remove palladium. The filtrate was worked-up with ethyl acetate and water, and then ethyl acetate layers were dried with MgSO$_4$. Combined organic layers were evaporated under a reduced pressure to remove most of the solvent and then filtered to obtain a first brown solid product. After the filtrate was evaporated under a reduced pressure to remove the solvent, the residue was dissolved in a small amount of ethyl acetate, to which n-hexane was added to induce crystallization. The resulting solid was filtered to obtain a second brown solid product. After the filtrate was again evaporated under a reduced pressure, the residue was dissolved in a small amount of ethyl acetate, to which n-hexane was added to induce crystallization. The resulting solid was filtered to obtain a third brown solid product. The obtained first to third products were combined and then dried, to afford N,N-di-naphtalen-1-yl-terphenyl-4,4'-diamine-d12 with an yield of 78%.

(4) Preparation of the desired product HIL-1

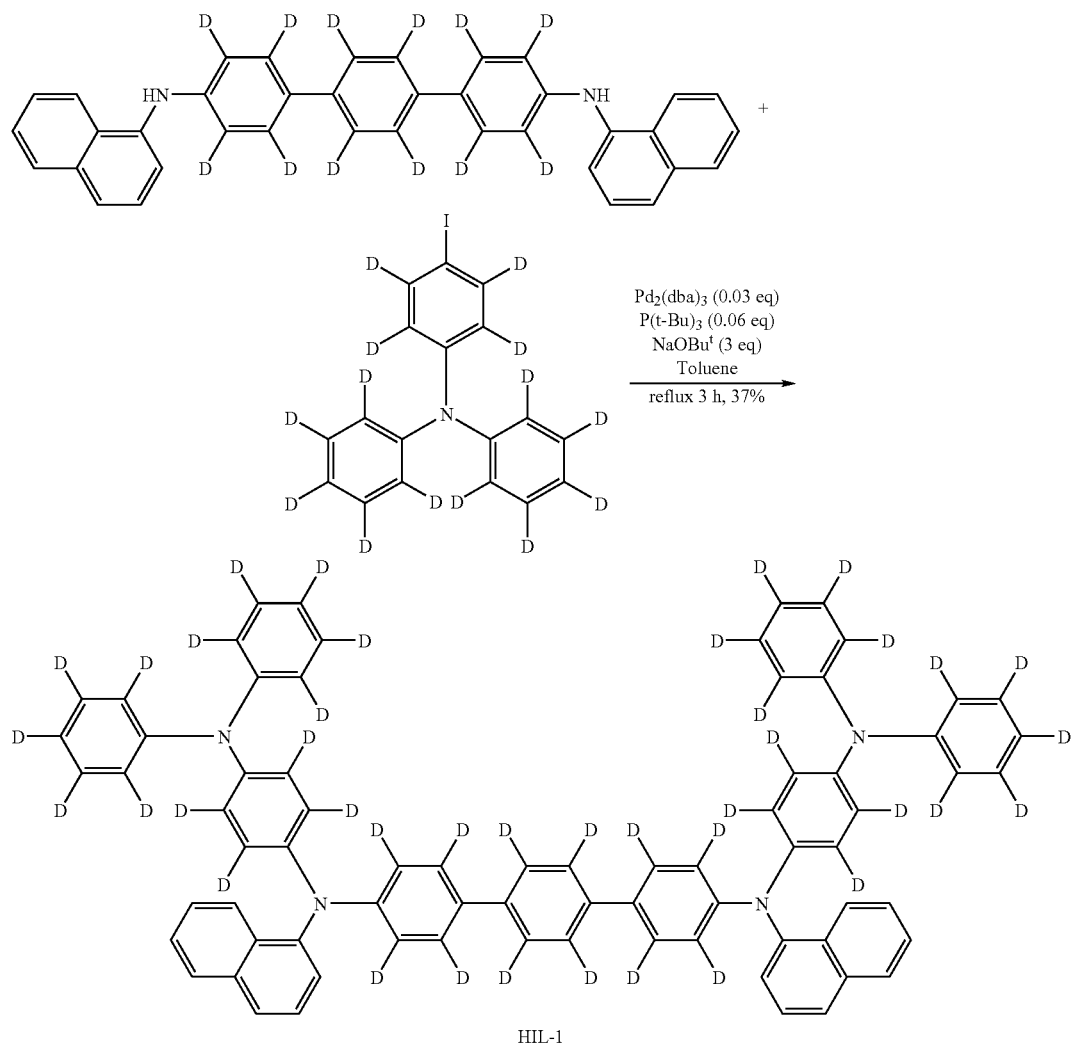

2.9 g (5.53 mmol) of the N,N-di-naphtalen-1-yl-terphenyl-4,4'-diamine-d12 and 4.3 g (11.1 mmol) of (4'-iodophenyl)-diphenylamine-d14 were dissolved in 20 mL of toluene, to which 0.15 g (0.166 mmol) of tris(benzylidene acetone dipalladium) was added under a nitrogen atmosphere. To the resulting mixture, 0.07 g (0.332 mmol) of P(t-Bu)$_3$, followed by 0.64 g (6.64 mmol) of NaOBu$^t$ were added. The reaction solution was refluxed while stirring for 3 hours. When the reaction was completed, the reaction solution was filtered by a thin silica gel pad so as to remove palladium. The filtrate was evaporated under a reduced pressure and then purified by a chromatography using 40% dichloromethane/n-hexane, to obtain a pale yellow solid product. The solid was dissolved in a small amount of dichloromethane and then crystallized using n-hexane, to obtain 2.3 g of the desired product (HIL-1) as a clean pale yellow solid (yield: 37%). The structure of the product was identified by mass spectral data.

FAB mass spectral data: molecular weight peak—Found: 1021, Calculated: 1021.

UV and PL data of the product (HIL-1) are presented in FIG. 1.

Example 2

(1) Preparation of N,N-di-naphtalelen-1-yl-anthracenyl-9,10-diamine

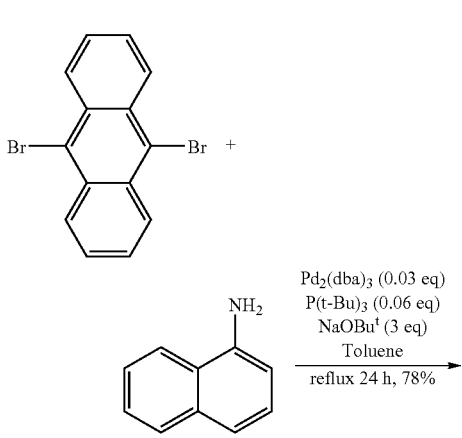

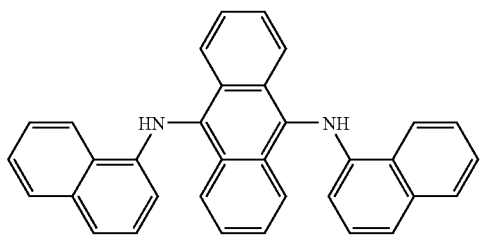

5 g (14.9 mmol) of 9,10-dibromoanthracene and 4.26 g (29.8 mmol) of 1-aminonaphtalene were dissolved in 200 mL of toluene, to which 0.41 g (0.447 mmol) of tris(benzylidene acetone dipalladium) was added under a nitrogen atmosphere. To the resulting mixture, 0.18 g (0.89 mmol) of P(t-Bu)$_3$, followed by 1.72 g (17.9 mmol) of NaO-t-Bu were added. The reaction solution was refluxed while stirring for 24 hours. When the reaction was completed, the reaction solution was filtered at a high temperature through a thin silica gel pad to remove palladium. The filtrate was worked-up using ethyl acetate and water. Ethyl acetate layers were dried with MgSO$_4$ and then evaporated under a reduced pressure to remove most of the solvent. The residue was filtered to obtain a first brown solid product. After the filtrate was again evaporated under a reduced pressure, the residue was dissolved in a small amount of ethyl acetate, and n-hexane was added so as to induce crystallization. The generated solid was filtered to obtain a second brown solid product. The filtrate was again evaporated under a reduced pressure, the residue was dissolved in a small amount of ethyl acetate, and n-hexane was added so as to induce crystallization. The generated solid was filtered to obtain a third brown solid product. The obtained first to third products were combined and then dried, to afford N,N-di-naphtalen-1-yl-anthracenyl-9,10-diamine with an yield of 68%.

(2) Preparation of the desired product HIL-2

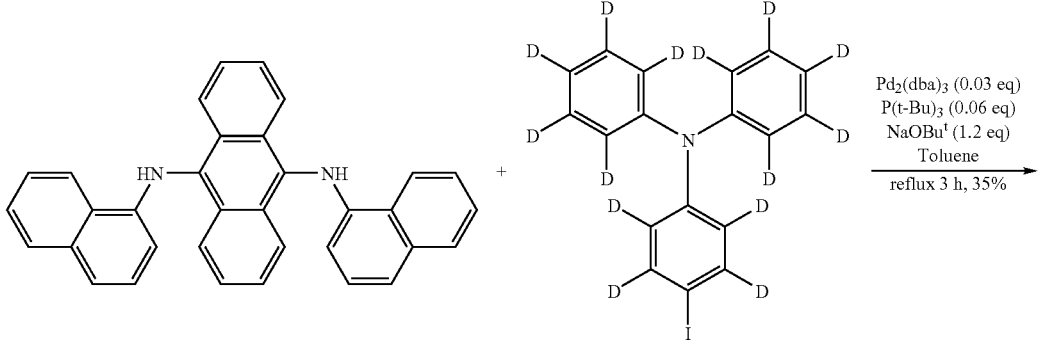

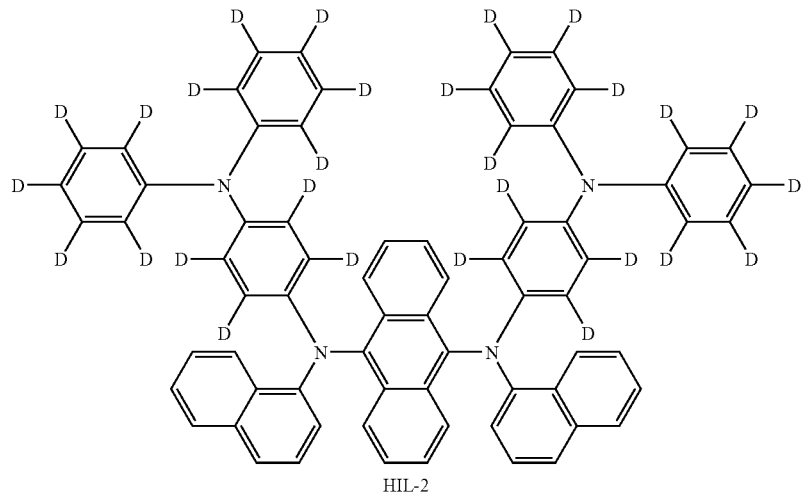

2.0 g (4.34 mmol) of N,N-di-naphtalen-1-yl-anthracenyl-9,10-diamine and 3.3 g (8.68 mmol) of (4'-iodophenyl)-diphenylamine-d14 prepared as described in step (1) and (2) of Example 1 were put into toluene, to which 0.12 g (0.130 mmol) of tris(benzylidene acetone dipalladium) was added under a nitrogen atmosphere. To the resulting mixture, 0.08 g (0.260 mmol) of P(t-Bu)$_3$, followed by 0.05 g (29.9 mmol) of NaOBu$^t$ were added. The reaction solution was refluxed while stirring for 3 hours. When the reaction was completed, the reaction solution was filtered by a thin silica gel pad so as to remove palladium. The filtrate was evaporated under a reduced pressure, and the residue was purified by a chromatography using 30% dichloromethane/n-hexane, to obtain a pale yellow solid. This solid was dissolved in a small amount of dichloromethane and then crystallized by adding n-hexane, to obtain 1.45 g of the desired product (HIL-2) as a clean pale yellow solid (yield: 35%). The structure of the product was identified by mass spectral data.

FAB mass spectral data: molecular weight peak—Found: 957, Calculated: 958

A device of a structure shown in Table 1 below was fabricated using the final product HIL-1 prepared in Example 1 as a material of a hole-injecting layer, and its characteristics were evaluated. As a result of experiments using C-545T (product of Idemitsu Co.) as a green luminescent material, an EL spectrum shown in FIG. 2 was obtained. As can be seen from FIG. 4, the device using the compound of Example 1 showed a half life of 273 hours. Referring to FIGS. 5 and 6, when hydrogen atoms were substituted with deuterium atoms, the current density and luminance relative to the voltage were similar to or higher than those of the compound without deuterium substitution. Referring to FIGS. 7 and 8, when hydrogen atoms were substituted with deuterium atoms, the current efficiency and power efficiency relative to luminance were improved compared with those of the the compound without deuterium substitution.

TABLE 1

| | Hole injecting layer | Light emitting layer | Hole transferring layer | Electron transferring layer | Electron injecting layer | Cathode |
|---|---|---|---|---|---|---|
| Material | HIL-1 | NPB | Alq3 + C 545T | Alq3 | LiF | Al |
| Thickness (Å) | 400 | 150 | 295 + 6 | 300 | 10 | 2000 |
| | 500 | 150 | 295 + 6 | 300 | 10 | 2000 |
| | 600 | 150 | 295 + 6 | 300 | 10 | 2000 |
| Deposition Temperature (° C.) | 330 | 270 | 280/150 | 280 | — | — |

According to the present invention, a novel deuterated aryl amine compound capable of enhancing thermal stability, luminance, hole transferring capability, light emitting efficiency, etc., a preparation method thereof, and an organic light emitting diode using the same are provided.

As shown in FIGS. 6 to 8, in the novel deuterated aryl amine compound of the present invention, luminance, power efficiency, the current efficiency, etc. were enhanced, compared with the compound without deuterium substitution.

As the present invention may be embodied and modified in several forms without departing from the spirit or essential characteristics thereof, it should also be understood that the above-described embodiments are not limited by any of the details of the foregoing description, unless otherwise specified, but rather should be construed broadly within its spirit and scope as defined in the appended claims, and therefore all changes and modifications that fall within the metes and bounds of the claims, or equivalence of such metes and bounds are therefore intended to be embraced by the appended claims.

The invention claimed is:

1. A deuterated aryl amine compound consisting essentially of, the compound represented by Formula HIL-1 or Formula HIL-2:

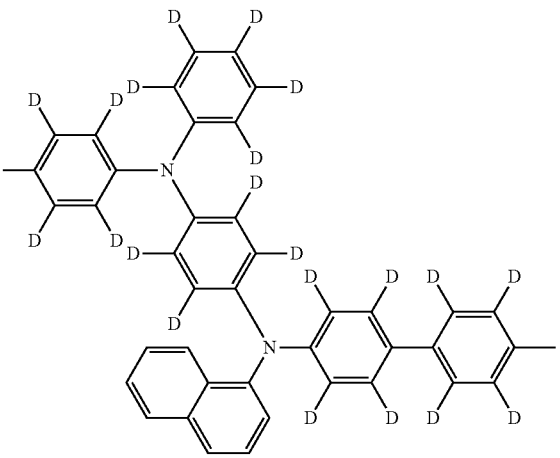

Formula HIL-1

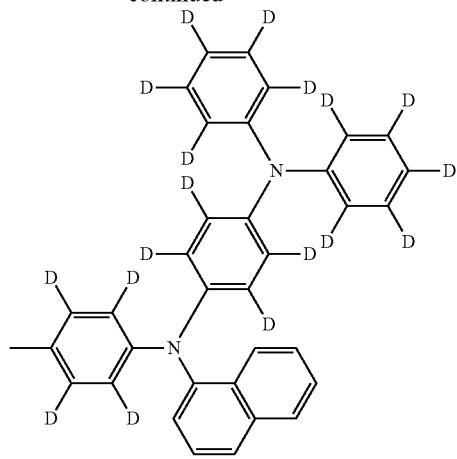

-continued

-continued

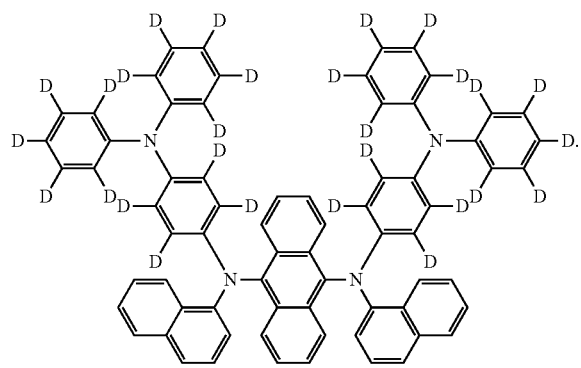

Formula HIL-2

2. An organic light emitting diode, comprising a hole injecting layer and a light emitting layer, said hole injecting layer consisting essentially of the deuterated aryl amine compound according to claim 1.

3. A method for preparing the aryl amine compound of claim 1, comprising:
(1) reacting a compound of Formula 6 with a compound of Formula 7a and/or 7b, followed by halogenating the resulting product, to obtain compounds represented by general formulae $Ar^1$—Y and $Ar^2$—Y;
(2) reacting any one compound shown in Formula 8 with a compound of Formula 9, to obtain a compound of Formula 5; and
(3) reacting the compound of Formula 5 with compounds represented by general formulae $Ar^1$—Y and $Ar^2$—Y, to obtain the compound of Formula 1:

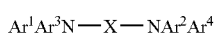

Formula 1

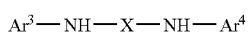

Formula 5

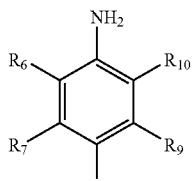

Formula 6

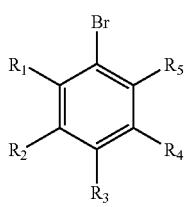

Formula 7a

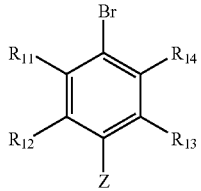

Formula 7b

-continued

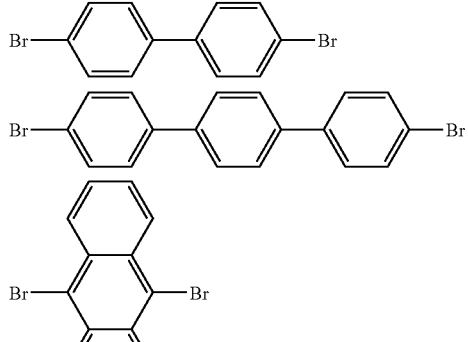

Formula 8

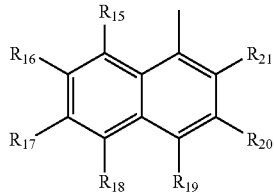

Formula 9 wherein $Ar^1$ and $Ar^2$ are respectively a diphenylaminophenyl group represented by Formula 2 and are identical to or different from each other;

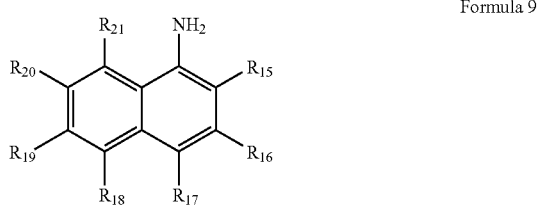

Formula 2

$Ar^3$ and $Ar^4$ are respectively a naphthyl group represented by Formula 3 and are identical to or different from each other;

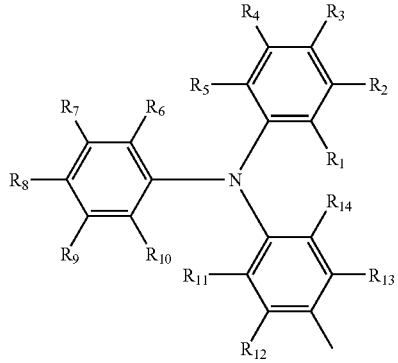

Formula 3

$R_1$ to $R_{21}$ are respectively selected from the group consisting of hydrogen, deuterium, $C_1$-$C_{30}$ alkyl group and a halogen atom, provided that at least one of $R_1$ to $R_{21}$ are deuterium atom;

X is selected from the species of structures shown in Formula 4 and may be unsubstituted or substituted with at least one deuterium atoms;

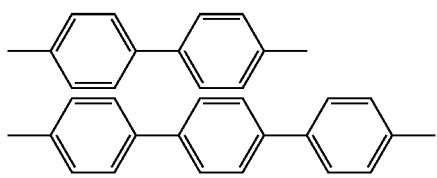

Formula 4

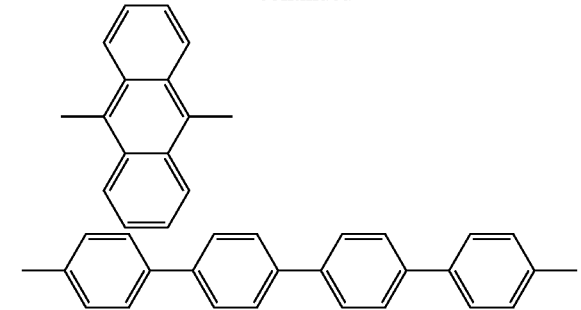

Y is a halogen atom selected from F, Cl, Br and I; and
Z is hydrogen or deuterium.

* * * * *